(12) United States Patent
Butler et al.

(10) Patent No.: US 8,264,239 B2
(45) Date of Patent: Sep. 11, 2012

(54) GUIDED WAVE CUTOFF SPECTROSCOPY USING A CYLINDRICAL MEASUREMENT CELL

(75) Inventors: Darrel Thomas Butler, Austin, TX (US); Tom Lee Erb, Austin, TX (US)

(73) Assignee: Thermo Fisher Scientific, Coon Rapids, MN (US)

( * ) Notice: Subject to any disclaimer, the term of this patent is extended or adjusted under 35 U.S.C. 154(b) by 402 days.

(21) Appl. No.: 12/462,239

(22) Filed: Jul. 30, 2009

(65) Prior Publication Data

US 2011/0025347 A1  Feb. 3, 2011

(51) Int. Cl.
*G01R 27/02* (2006.01)
(52) U.S. Cl. ........ 324/639; 324/637; 324/638; 324/640; 324/641; 324/642
(58) Field of Classification Search ........... 324/637–646
See application file for complete search history.

(56) References Cited

U.S. PATENT DOCUMENTS

| | | | |
|---|---|---|---|
| 3,500,182 A * | 3/1970 | Bilbrough et al. | ............ 324/640 |
| 3,962,466 A * | 6/1976 | Nakabayashi | .................. 426/60 |
| 4,630,316 A | 12/1986 | Vaughan | |
| 5,455,516 A * | 10/1995 | Jean et al. | ...................... 324/639 |
| 6,905,872 B1 * | 6/2005 | Rindt | ........................... 435/287.5 |
| 2004/0202573 A1* | 10/2004 | van den Brink et al. | ..... 422/68.1 |
| 2009/0000393 A1* | 1/2009 | Nyfors et al. | .............. 73/861.19 |

* cited by examiner

*Primary Examiner* — Timothy J Dole
*Assistant Examiner* — Son Le
(74) *Attorney, Agent, or Firm* — David George Johnson (57) ABSTRACT

A cylindrical waveguide (1) used for analyzing a flowing stream of corn masa (18) using a guided microwave spectroscopy (GMS) process. The waveguide (1) includes opposed spaced apart plates (2, 5) that each define a plane within the waveguide housing (3) that is parallel to the direction (47) of corn masa flow through the waveguide. The housing (1) includes two opposed frames (7, 19) that each surround an aperture (6) that permits access to the region between the waveguide plates (2, 5). A microwave probe assembly (81) is mounted at each frame (7, 19) to permit the radiation and reception of electromagnetic waves within the housing (1) as required to perform the GMS process. A temperature probe (51) is inserted into the interior of the housing (1) at a fitting (13). In an actual installation a y-shaped assembly (89) can be used to divide the corn masa flow into two separate paths with one path containing the waveguide (1). A diverter vane (93) within the y-shaped assembly permits flow to be equalized within the two separate flow paths.

4 Claims, 12 Drawing Sheets

GUIDED WAVE CUTOFF SPECTROSCOPY USING A CYLINDRICAL MEASUREMENT CELL

BACKGROUND OF THE INVENTION

1. Field of Invention

This invention pertains generally to the field of guided microwave spectroscopy and more particularly to measurement cells used to implement such spectroscopy techniques.

2. Description of Prior Art

Figure 2:
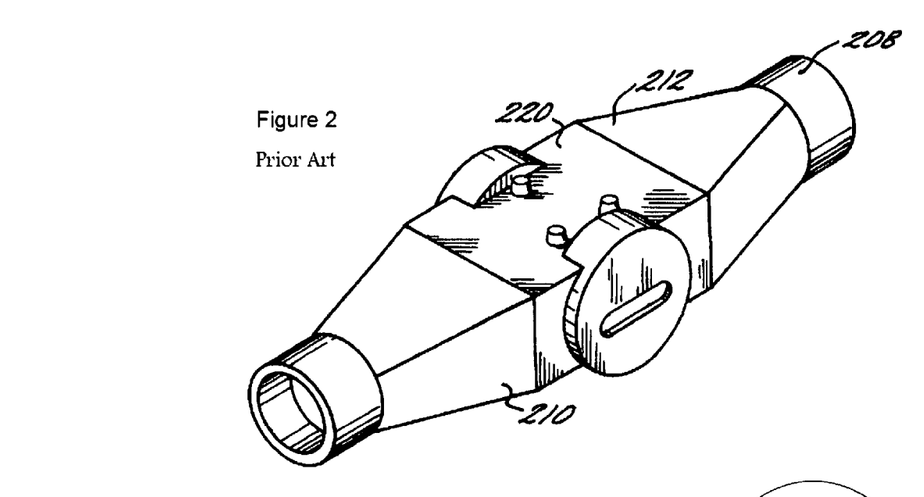
FIG. 2 is an isometric view of a prior art frequency sensitive measurement cell.

Guided microwave spectroscopy (GMS) is a system that combines microwave spectral technology with a waveguide to provide precise compositional analysis of flowable materials, which can either be slurry or a gas. In particular, the GMS system permits the measurement of changes in the dielectric constant and the conductivity of the flowable material, thereby allowing the moisture content and other constituent properties to be inferred. An exemplary embodiment of GMS technology is disclosed in U.S. Pat. No. 5,455,516 entitled METER AND METHOD FOR IN SITU MEASUREMENT OF THE ELECTROMAGNETIC PROPERTIES OF VARIOUS PROCESS MATERIALS USING CUTOFF FREQUENCY CHARACTERISTIZATION AND ANALYSIS, issued to Jean et al. on Oct. 3, 1995. FIG. 2 depicts the frequency sensitive measurement cell 220 that is used for performing GMS measurements as disclosed in the Jean patent. Measurement cell 220 is connected in line with and forms a portion of a conduit carrying the flowable material being examined. The Jean device includes transition members 210 and 212 which are necessary to convert the circular cross section of the material processing conduit 208 into the rectangular cross section of the measurement cell 220. For highly viscous materials or materials such as a gas transported under relatively high pressure, the transition members introduce discontinuities in the mass flow rate of the material, affecting the accuracy of any measurement derived from the GMS system as well as the integrity of the production line which is processing the material.

An example of a highly viscous flowable material is corn masa, which is a dough used for baking tortillas. A tortilla is a baked grain product which originated in Mexico and is now widely consumed throughout the world. As the demand for tortillas has grown, the methods and the apparatus for automatically producing tortillas in high volumes have become well known. In the conventional automated system, dough is produced by cooking whole corn and grinding it while in a wet state or by combining instant corn masa flour with water in a commonly available mixer. This dough is generally referred to as "masa". However, the term "masa" as used herein refers to this corn dough and other dough or slurry like materials having similar characteristics. The masa is often fed into an extruder which compresses the masa and outputs it in the form of a generally continuous stream to a pneumatic cutter. The pneumatic cutter chops the masa into generally cylindrical pieces, generally known as "logs". The logs are usually carried on a conveyor to a masa hopper, which gravity feeds the masa to several successive pairs of generally opposed, counter rotating cylindrical rollers for compression into a sheet having the thickness required for tortilla production. This "sheeted" masa is then cut into the desired tortilla shape by a commonly available rotary cutter, which usually cuts circles of varying diameter. The cut masa is then baked and/or fried, cooled, and packaged by commonly available commercial food processing equipment.

Figure 1:
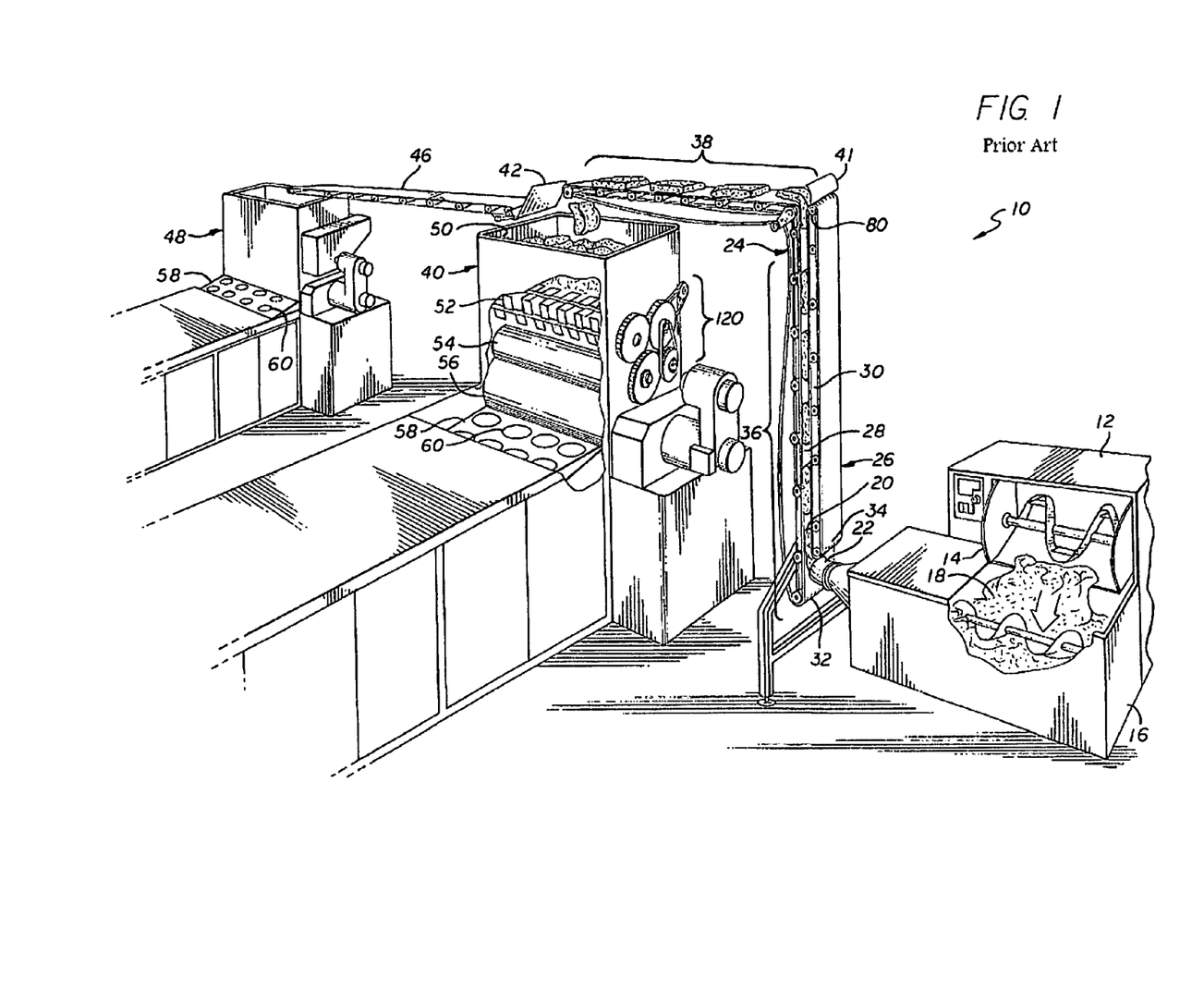
FIG. 1 is a perspective view of a prior art corn masa processing system.

Depicted in FIG. 1 is a masa handling system that is a part of a larger arrangement of apparatus intended for the commercial production of tortillas or other food having masa dough as an ingredient. The general arrangement of the masa handling system 10 includes a commonly available commercial mixer 12 that is located at the beginning of the production line. The mixer 12 has a pivoting door 14 which can rotate downward towards a masa extruder 16. The masa extruder 16 compresses the masa 18 and feeds a generally continuous masa stream 20 through a nozzle 22. Two vertically opposed and aligned endless belt separator conveyors 24 and 26 have moving surfaces 28 and 30, respectively, which face each other. The longitudinal ends 32 and 34 of separator conveyors 24 and 26 are mounted adjacent to the nozzle 22. One of the two separator conveyors 24 is "L" shaped and has a vertical section or portion 36 and a horizontal section or portion 38 which terminates above a masa hopper 40.

The vertical section 36 of the "L" shaped separator conveyor 24 extends longitudinally below the longitudinal end of the other separator conveyor, thereby providing a moving surface opposite from the nozzle 22. A deflector plate 41 is mounted on the end of the other separator conveyor 26. The separator conveyors 24 and 26 move the masa 18 to the masa hopper 40 which contains the sheeter assembly 120. The masa hopper 40 must be supplied with masa 18 periodically.

A selectively operable diverter gate 42, for periodically permitting replenishment of the masa hopper 40, is located adjacent to the end 44 of the horizontal section 38 of the "L" shaped separator conveyor 24. The diverter gate 42 is shown in its open position. When the diverter gate 42 is closed, its top surface forms a gravity slide that feeds material to a horizontal feed conveyor 46, which in turn feeds another masa hopper 48.

Each masa hopper 40 and 48 has a hollow inner gravity feeder portion 50 containing two counter rotating shafts 52 mounted above a pair of primary rollers 54. The primary rollers 54 are, in turn, mounted above a pair of counter rotating sheet rollers 56 and a common rotary cutter. A horizontal tortilla conveyor 58 is mounted below the rotary cutter and has tortillas 60 on its upper surface. The remainder of the system can include various combinations of commonly known and widely available commercial food processing apparatus such as an oven, a cooling rack, and a packaging system.

As can be seen in FIG. 1, the mass flow analysis of the masa would ideally be performed in the region of the nozzle 22, but such a measurement cannot introduce any significant impediment to the flow of the masa 18 without endangering the required constant and continuous supply of masa to the conveyors 26 and 24. The rectangular measurement cell and its associated cross sectional transitions as shown in FIG. 2 would be unsuitable for use in such a corn masa processing environment.

What is needed when processing masa, other highly viscous materials or a relatively high pressure material is the flat plate geometry of the Jean measurement cell residing within an existing circular conduit that would permit the use of the flat plate measurement cell while employing the GMS technique.

An example of a conduit using parallel plates within a circular conduit is disclosed in U.S. Pat. No. 3,500,182, entitled APPARATUS FOR AND A METHOD OF HIGH FREQUENCY ELECTROMAGNETIC MOISTURE MEASUREMENT IN HIGHLY VISCOUS PASTES AND SIMILAR MATERIALS, issued to Reed et al. on Mar. 10, 1970. The Reed device measures moisture by passing high frequency electromagnetic signals through the viscous material. The viscous material is constrained in a chamber having a pair of opposed boundary plates extending edge on in the direction of movement of the material to form a combining guide path for the signals. The signals are evaluated before and after traveling through the material to determine the moisture content of the material. However, the Reed device processes the data received quite differently than the GMS apparatus, the GMS system being adapted to analyze complex permittivity properties. Further, the Reed device utilizes a different frequency which precludes launching the electromagnetic energy into the matrix under test in the TE10 mode as required by the GMS system. U.S. Pat. No. 4,630,316, entitled TRANSITION BETWEEN RECTANGULAR AND RELATIVELY LARGE CIRCULAR WAVEGUIDE FOR A UHF BROADCAST ANTENNA, issued to Vaughan on Dec. 16, 1986 exposes the difficulty of propagating linearly polarized TE10 and circularly polarized TE11 electromagnetic energy in a single transmission path. The present invention addresses the foregoing problems.

SUMMARY OF THE INVENTION

The current invention is an improved apparatus and method for using the GMS waveguide cutoff frequency technique to characterize materials having relatively high viscosity or being processed under relatively high pressure. The present invention includes a measurement cell having a parallel plate waveguide in which the microwave energy travels laterally across the material flow path. This configuration is relatively unobtrusive to the material flow, thereby permitting the uniformity of material flow to be maintained. In some embodiments of the present invention, the presence of standing wave anomalies within the measurement cell is significantly reduced. Measurements performed with the cell of the present invention are typically more sensitive than those obtained with previous methods due to the availability of an arbitrarily long measurement path.

The present invention is described according to various embodiments of the measurement cell, including a straight pipe cell, a Z-type cell, a cell having skewed or offset microwave probe orientations and a cell in which the plates have nonrectangular geometries. In all embodiments the excitation and detection apertures are formed using fixed dielectric filled waveguide transitions, and the plates may be configured so as to be individually removable from the cell. The transitions interface with the cell so as to present a relatively uniform cylindrical wall with essentially the same shape and dimensions as the remaining tubing used in the material transport system. In the Z-type embodiment, the excitation and detection apertures reside at the elbows of the Z and substantially face each other. In the skewed probe geometry embodiment, the apertures are both substantially perpendicular to the direction of material flow but are not coaxially aligned.

In a preferred embodiment of the invention, the device provides data relating to the moisture content of the masa dough material. An electronic feedback loop, which can be either analog or digital in nature, is utilized to adjust the amount of water being added to the masa dough or other material in order to maintain desired moisture content.

A Y-shaped pipe transition is employed to permit drag equalization and adjustment of the masa flow. One leg of the Y-shaped pipe includes the actual measurement cell, while the other leg of the pipe includes a drag producing element to simulate the amount of flow obstruction presented by the actual cell. The measurement cell typically includes an eight inch pipe or conduit within which are welded two parallel, flat plates which serve as the waveguides for the radiated microwave energy. An adjustable diverter vane resides near the junction of the Y-shaped pipe to permit precise control the relative flow between the diverging pipe sections.

DETAILED DESCRIPTION OF THE PREFERRED EMBODIMENTS

Figure 5:
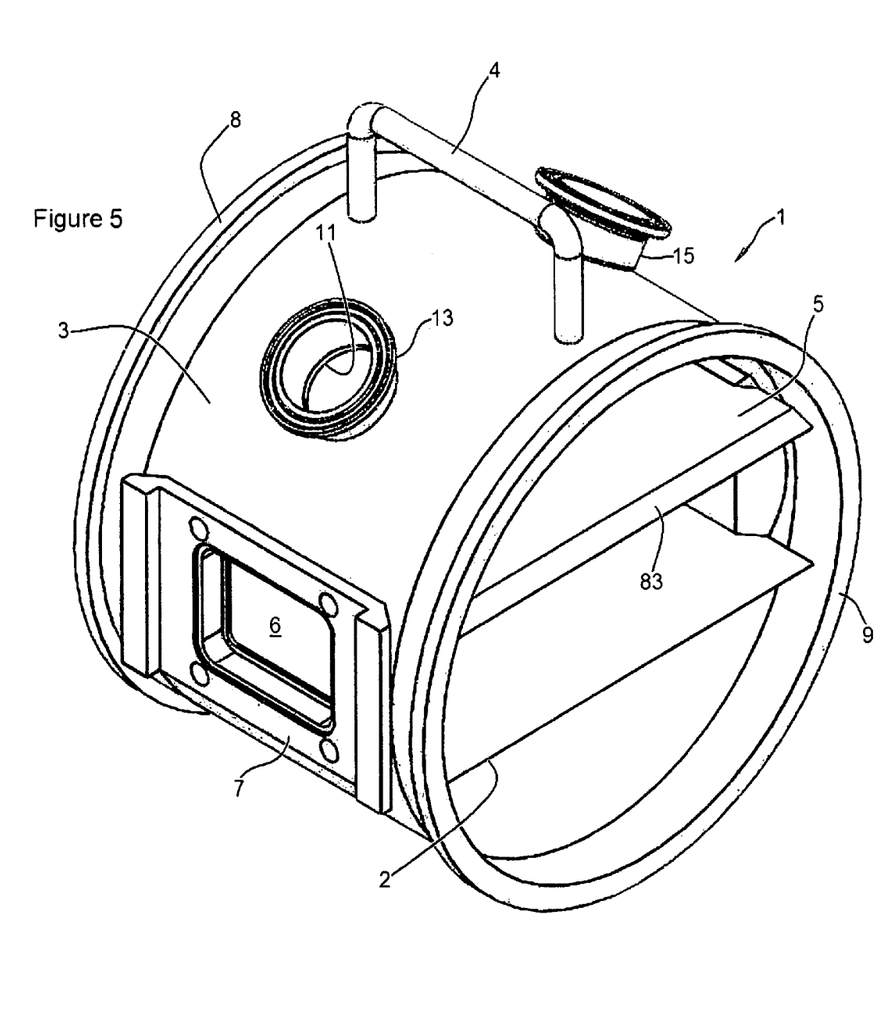
FIG. 5 is a perspective view of the cylindrical measurement cell depicted in FIG. 4.

Referring to FIG. 5, a cylindrical measurement cell constructed according to the principles of the present invention is shown generally at 1. The cell 1 includes a first plate 2 which is mounted within a cylindrical housing 3. Mounted substantially parallel to the first plate 2 is a substantially identical second plate 5. One or both of the plates 2 and 5 may be formed to include a beveled leading edge 83 to reduce resistance to a flowing product stream, and one or both plates may be individually removed from the housing 3. The spacing between the plates 2 and 5 determines the cutoff frequency above which radiated microwave energy may not be usefully employed using the GMS analysis technique and is defined by the formula:

$$f_c = \frac{c}{2a\sqrt{\varepsilon'}}$$

where $f_c$ is the cutoff frequency,
"a" is the distance between plates 2 and 5,
"c" is equal to the velocity of light, and
$\varepsilon'$ is the dielectric constant of a material flowing between plates 2 and 5.

The housing 3 is typically made of stainless steel and includes a handle 4 to facilitate manipulation of the waveguide during the performance of installation and maintenance procedures. Formed within the housing 3 is a first substantially rectangular aperture 6 that is defined and bordered by a frame 7. The rectangular aperture 6 permits electromagnetic energy to pass into an interior region of the housing 3.

Figure 7:
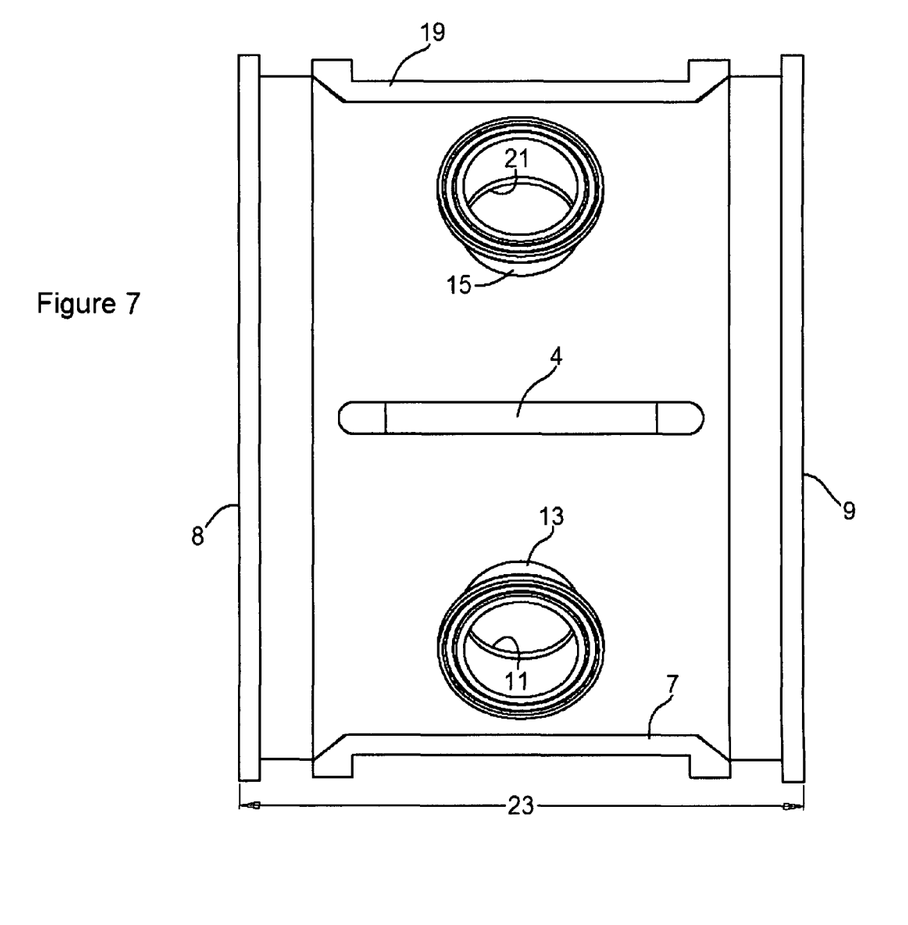
FIG. 7 is a top plan view the cylindrical measurement cell depicted in FIG. 6.

Since the cell 1 is intended for mounting as a section of a longer conduit, a first ferrule 8 and a second ferrule 9 are mounted at opposite ends of the housing 3 so as to be substantially parallel to each other and substantially perpendicular to the planes defined by the first plate 2 and the second plate 5. Referring also to FIG. 7, a first circular aperture 11 surrounded by a first fitting 13 is formed within the housing 3 to permit the insertion of a sensor probe. A second fitting 15 is associated with a second circular aperture 21 which permits access to the interior of the housing 3 for the purpose of collecting a sample from the measurement cell 1 for external primary method lab analysis.

Figure 6:
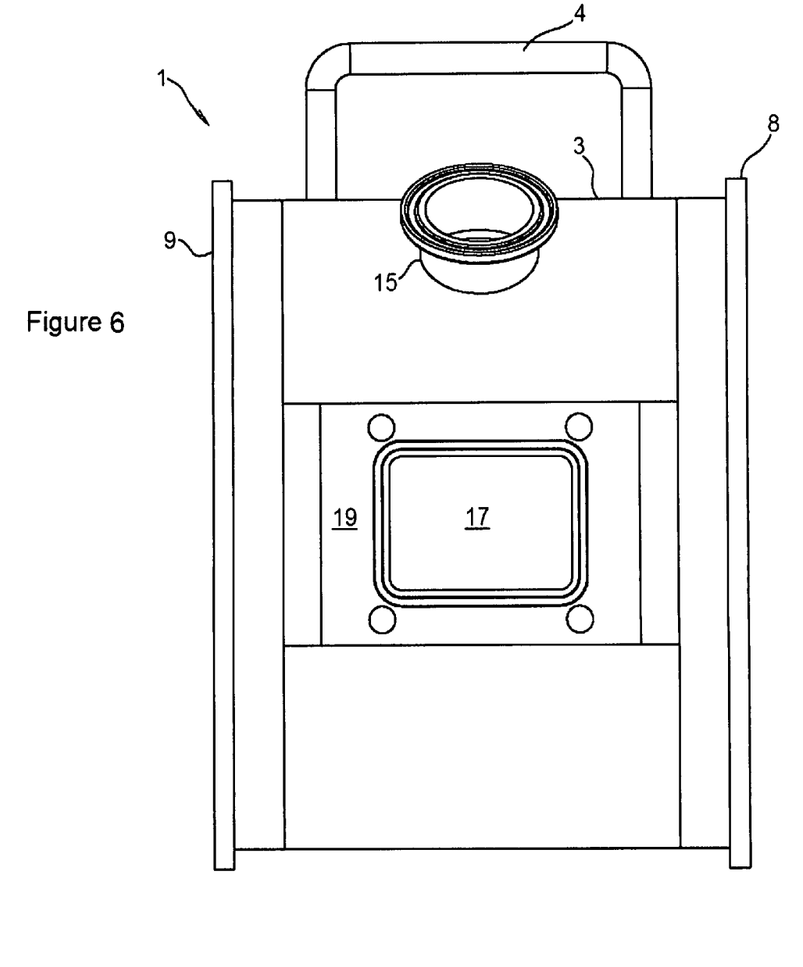
FIG. 6 is a right side elevation view of the cylindrical measurement cell depicted in FIG. 5.

As seen in FIG. 6, the cylindrical measurement cell 1 also includes a second substantially rectangular aperture 17 that is defined and bordered by a frame 19. The second rectangular aperture 17 is substantially parallel and exactly dimensioned to conform to the parameters of the first aperture 6. The second rectangular aperture 17 permits electromagnetic energy that is introduced into an interior region of the housing 3 via aperture 6 to exit the interior of the housing 3 and be detected by a probe or other suitable sensor.

Figure 3:
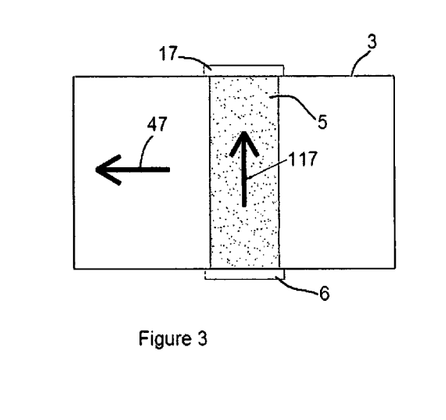
FIG. 3 is a top plan schematic view of a first embodiment of a measurement cell constructed according to the principles of the present invention.
Figure 4:
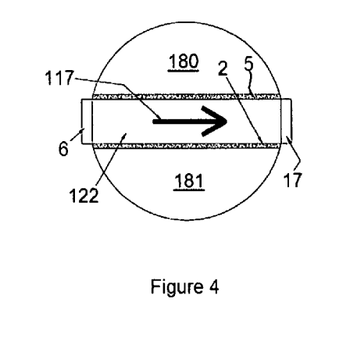
FIG. 4 is a side elevation schematic view of the measurement cell depicted in FIG. 3.
Figure 8:
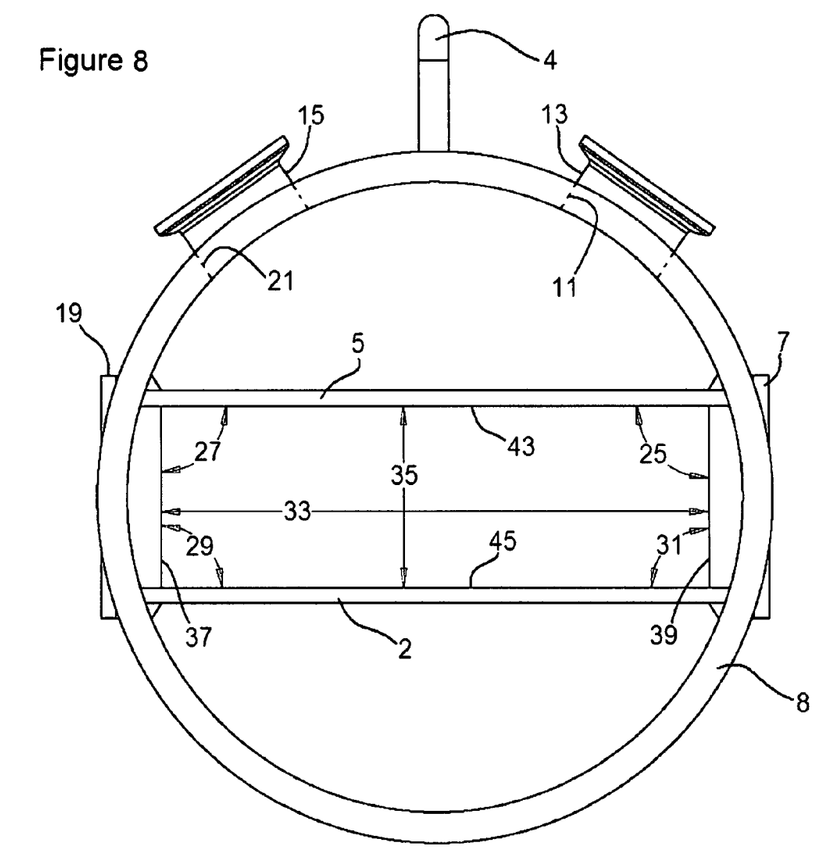
FIG. 8 is a front elevation view of the cylindrical measurement cell depicted in FIG. 7.

FIGS. 7 and 8 depict the overall symmetry of the measurement cell 1. The circular apertures 11 and 21 are substantially equally spaced with respect to the handle 4, as are the rectangular aperture frames 7 and 19. In a preferred embodiment, the distance 23 between the opposed ferrules 8 and 9 is approximately 6.75 inches. The distance 33 between the rear surface 37 of frame 19 and the rear surface 39 of frame 7 is approximately 6.90 inches. The distance 35 between the top surface 45 of first plate 2 and the bottom surface 43 of second plate 5 is approximately 2.25 inches. FIGS. 3 and 4 depict the region 122 residing between plates 2 and 5 through which material flows in the direction of arrow 47 and through which electromagnetic energy is radiated in the direction of arrow 117. The directions of material flow and electromagnetic energy propagation are substantially orthogonal. Bottom surface 43 forms an angle 27 with the rear surface 37 of approximately ninety degrees. Angle 25 formed between bottom surface 43 and rear surface 39 is also approximately ninety degrees.

The angle 29 formed between rear surface 37 and top surface 45 is approximately ninety degrees, as is the angle 31 residing between rear surface 39 and top surface 45.

Figure 9:
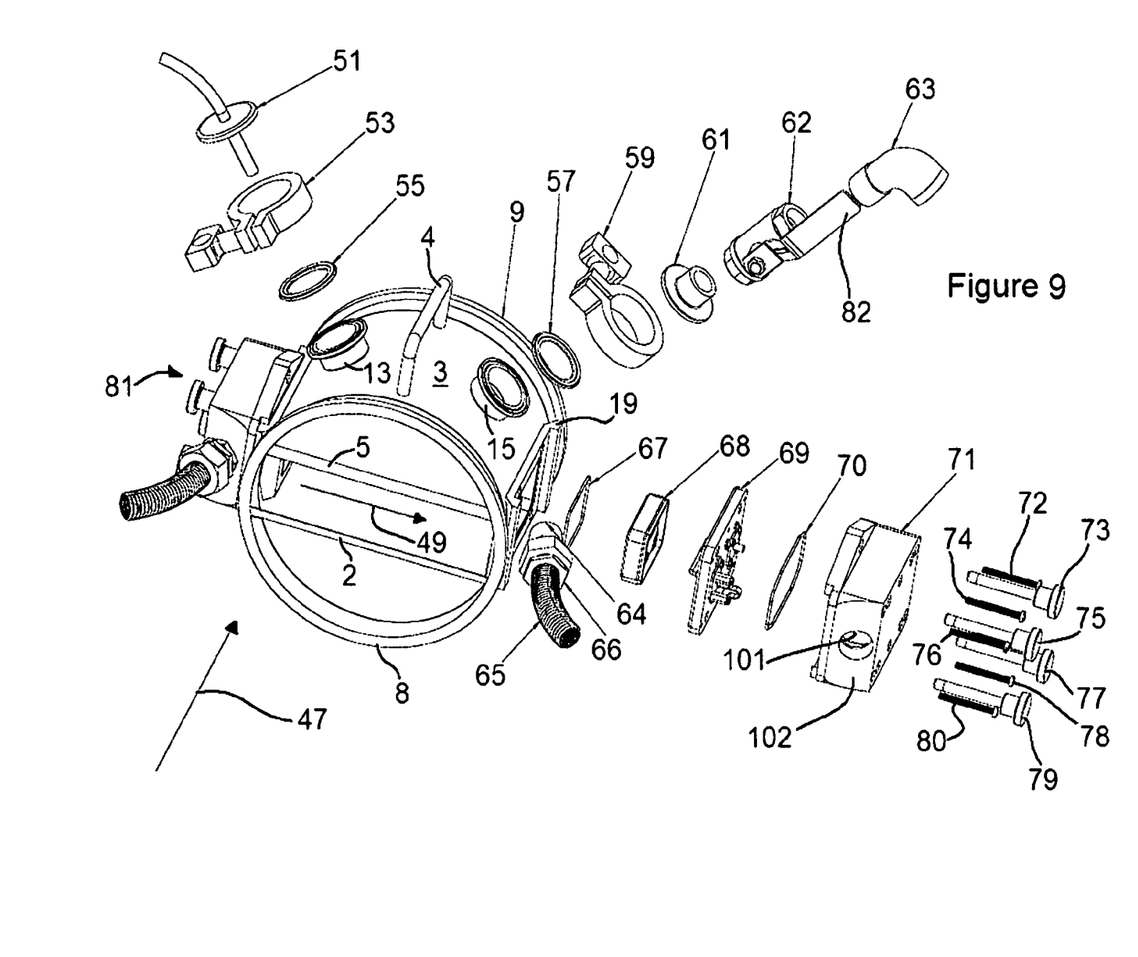
FIG. 9 is an exploded perspective view of an assembly including the cylindrical measurement cell constructed according to the principles of the present invention.

The cylindrical measurement cell 1 is part of the larger assembly depicted in FIGS. 9. Corn masa or other viscous product to be analyzed using the guided microwave spectroscopy (GMS) principle enters the waveguide by traveling in the direction of arrow 47, causing some of the product to pass between the plates 2 and 5, with the remaining product passing above plate 5 and beneath plate 2. A resistance temperature detector 51 is inserted into the waveguide via either the first fitting 13 or the second fitting 15, the detector 51 being secured to the fitting 13, for example, with the clamp 53 and gasket 55. The real time temperature characteristics of the material passing through the waveguide should be constantly monitored insofar as the dielectric properties of the process material being measured via the GMS technique tend to vary with temperature. A sample of the processed corn masa within the cell 1 may be examined via fitting 15, for example, via the pipe fitting 63. A ball valve 62 operable by handle 82 is interconnected to the pipe fitting 53. An adapter 61 fits into the ball valve 62 permitting the valve to be fastened to the second fitting 15 by means of a clamp 59 and gasket 57.

The GMS probe assembly 81 is fastened to the frame 7. A substantially identical probe assembly is affixed to the frame 19, with one probe functioning as the launching probe and the oppositely disposed probe performing the signal interception function. As depicted in FIGS. 3 and 4, the electromagnetic energy travels generally in the direction of arrow 117, being launched through the aperture 6 and being intercepted after passing through the aperture 17. The actual probe element 69 is seen to abut transparent process seal 68 which mates with an O-ring 67 that is pressed against frame 19. Another O-ring 70 is located between the probe element 69 and the probe cover 71. The probe cover 71 is attached to the probe element 69 by means of machine screws 72, 74, 76, 78 and 80. The entire probe assembly is affixed to the frame 19 by means of clamping knobs 73, 75, 77 and 79, which permit removal of the probe frame the frame without the need to actually disassemble the probe assembly.

Electromagnetic energy is introduced or removed from the probe 69 via a conduit 65, which is affixed to the probe cover 71 by means of a nut 66 and coupling 64. An orifice 101 that is compatibly dimensioned to receive the coupling 64 is formed within the sidewall 102 of the probe cover 71.

Figure 10:
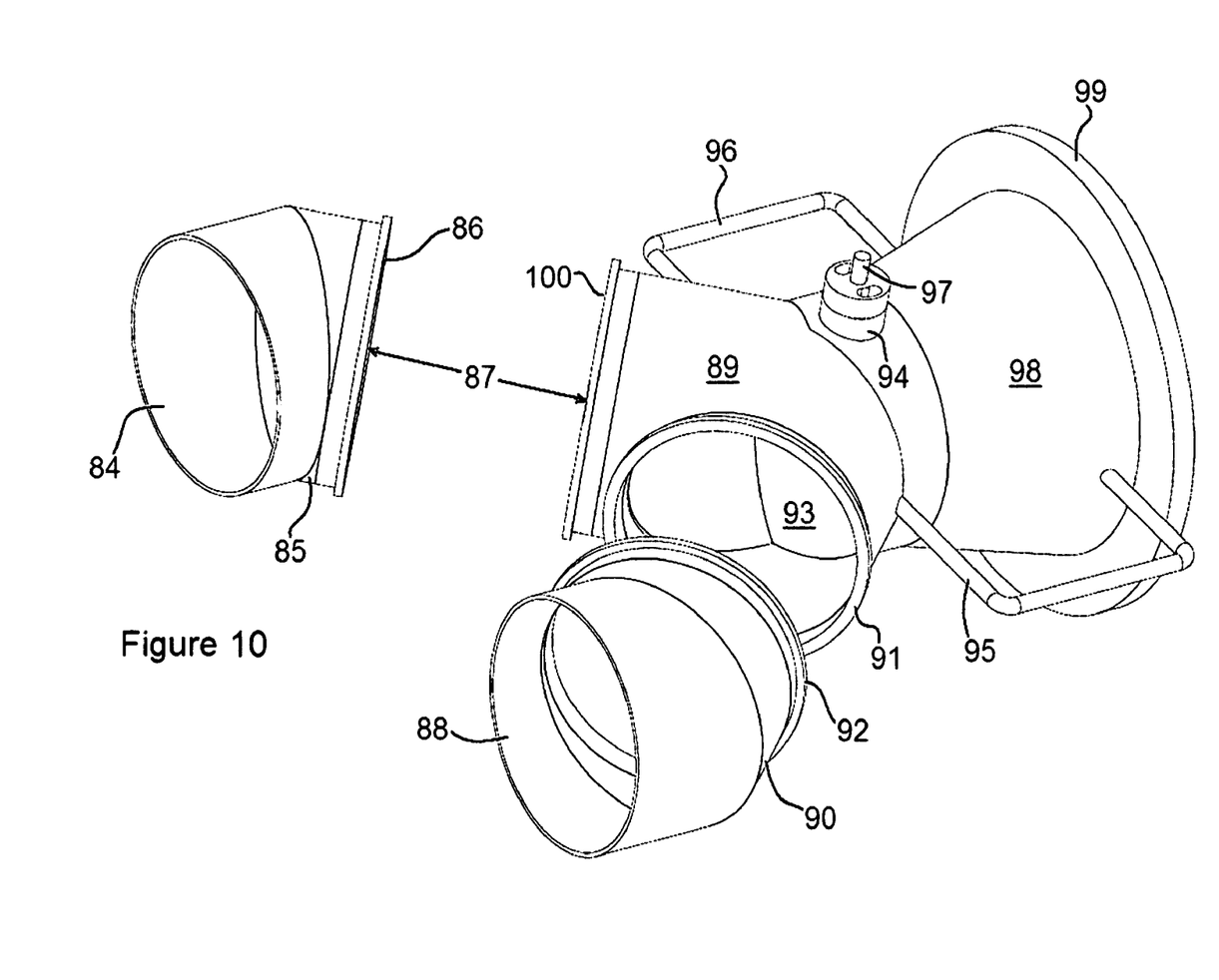
FIG. 10 is an exploded perspective view of a flow balancing assembly constructed according to the principles of the present invention.
Figure 11:
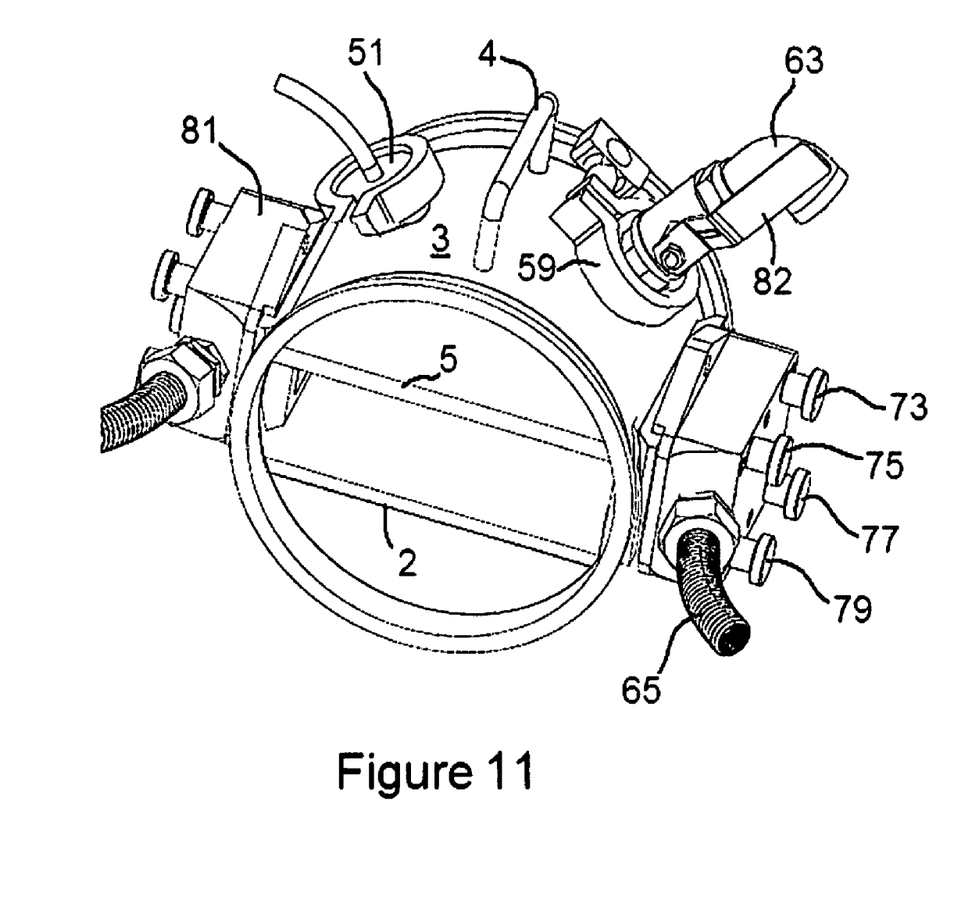
FIG. 11 is a perspective view of the assembly including the cylindrical measurement cell illustrated in FIG. 9.

When the cylindrical measurement cell 1 is utilized in a corn masa processing operation the high viscosity of the corn masa product creates a retarding force within the waveguide. In an effort to process the product at the highest rate possible and permit the replacement and servicing of the GMS probe assemblies, the measurement cell 1 is typically placed in one branch of a y-shaped fitting as illustrated in FIG. 10. The cell 1 is mounted within region 87 between the flange 86 and the flange 100. The flange 86 is part of an offset 85 which is affixed to the first processing pipe 84. A second processing pipe 88 is attached to an offset 90 that terminates at flange 92. Mounted between flange 92 and the flange 91 is a dummy cell that is substantially identical to the cylindrical cell 1 but lacking the actual GMS probe assemblies 81. While plates similar to plates 2 and 5 may be placed within the dummy cell, any obstruction having similar flow restricting characteristics may be employed. The flanges 92 and 100 define the two branches of the y-assembly 89 which is part of the collar 98 that is attached to a bin similar to the masa production bin 16 by means of the flange 99. The collar includes two handles 95 and 96, as well as a diverter vane 93. A rotatable handle 97 supported within bearing 94 permits positioning of the vane 93 in a position that equalizes flow between the two production pipes 84 and 88.

Figure 12:
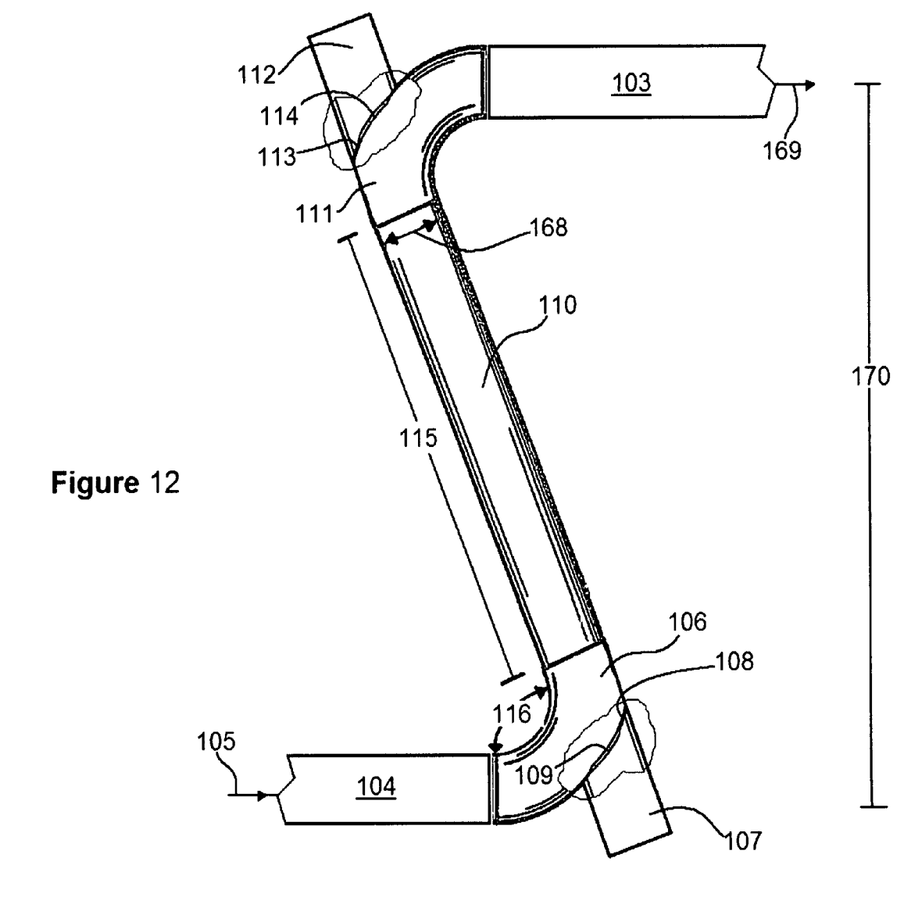
FIG. 12 is a top plan view of a second embodiment of a cylindrical measurement cell constructed according to the principles of the present invention

In some situations the retarding force exerted by the plates 2 and 5 may be so great as to require the elimination of the plates altogether. Referring to FIG. 12, alternate measurement cell geometry is disclosed that utilizes a circular measurement cell 110 that may be inserted between material processing pipes 103 and 104. The highly viscous material initially flows in the direction of arrow 105 before encountering a first elbow 106 that diverts the entire process material flow through an angle 116 and into the circular cell 110.

After traveling the length 115 of the measurement cell 110, a second elbow 111 redirects the material flow into the second processing pipe 103, causing the material to flow in the direction of arrow 169. The arrows 105 and 169 are not collinear and may not even be parallel, being laterally offset by the distance 170. The inside diameter 168 of the cell 110 is typically equal to the inside diameter of the process pipes 103 and 104.

In order to perform the GMS analysis of the material flowing through cell 110, a microwave probe and launching assembly 107 is affixed to the elbow 106. A microwave transparent process seal 109 is formed within the wall 108 of elbow 106 so as to permit electromagnetic energy to be emitted into the cell 110 and to propagate toward the second elbow 111. A microwave probe and signal interception assembly 112 is affixed to the second elbow 111, the assembly 112 being able to intercept the microwave energy through a substantially transparent process seal 114 formed within the second elbow wall 113. In this manner the length 115 may be selected to optimize the GMS analysis of a particular flowable material while eliminating the need to introduce any flow obstructions within the measurement cell 110.

Figure 17:
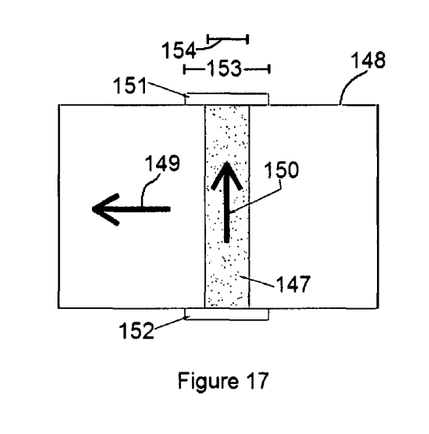
FIG. 17 is a top plan schematic view of a fifth embodiment of a cylindrical measurement cell constructed according to the principles of the present invention.
Figure 18:
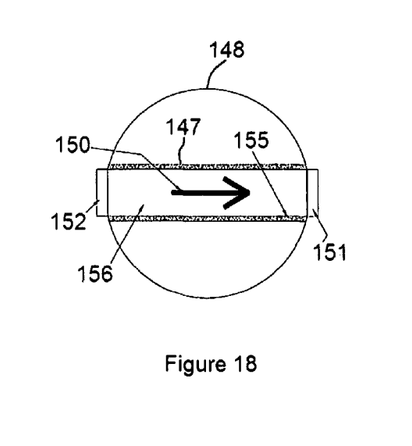
FIG. 18 is a side elevation schematic view of the cylindrical measurement cell depicted in FIG. 17.

The foregoing description of the preferred embodiments of the invention is subject to many variations. In particular, fittings and access ports in addition to the fittings 13 and 15 may be added to provide additional sensor and telemetry data regarding the product flow through the waveguide. The spacing 35 between the plates 2 and 5 as well as the dimensions of the plates may be varied as required for different operating frequencies and process materials used in the GMS process. For example, FIGS. 17 and 18 depict a measurement cell 148 used to analyze a process material traveling in the direction indicated by arrow 149. Electromagnetic energy is radiated through the launch aperture 152 generally in the direction of arrow 150 so as to pass through the reception aperture 151, each aperture 151, 152 having a width 153. The two waveguide plates 147 and 155 are spaced apart so as to define a region 156 through which the process material may pass. The process material is also free to pass above top plate 147 and beneath bottom plate 155.

The width 154 of each plate 147, 155 is less than the aperture width 153, creating a lower drag region 156 than would be possible if the plate width 154 was substantially greater.

While the housing 3 has been depicted as having a substantially circular cross section, other symmetrical ellipsoidal arrangements may be used. While the process material is typically free to pass above the top waveguide plate and beneath the lower waveguide plate, a relatively low viscosity material may permit the region 180 above the top plate and region 181 below the bottom plate to be blocked so as to require all of the process material to flow between the waveguide plates. Further, the path followed by the electromagnetic energy radiated through the measurement cell may follow a path which is not substantially perpendicular to the walls of the measurement cell. For example, the offset launch and intercept geometry depicted in FIGS. 13 and 14 may be utilized.

Figure 13:
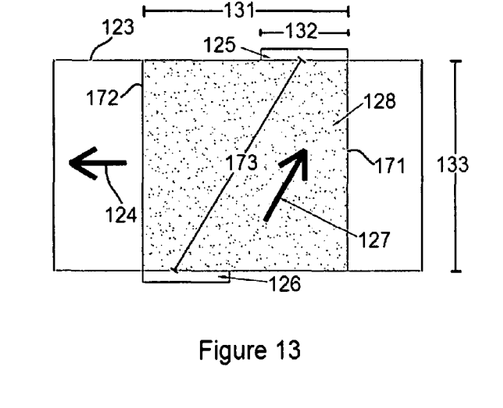
FIG. 13 is a top plan schematic view of a third embodiment of a cylindrical measurement cell constructed according to the principles of the present invention.
Figure 14:
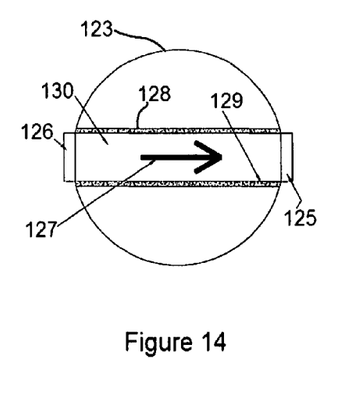
FIG. 14 is a side elevation schematic view of the cylindrical measurement cell depicted in FIG. 13.

In the offset launch and intercept arrangement of measurement cell 123 the radiated energy is launched by passing through a first aperture 126. The radiated microwave energy is intercepted after passing through region 130 occupied by the process material which is traveling in the direction of arrow 124. The radiated energy eventually reaches and travels through a second aperture 125 which is associated with an intercept probe assembly. While the beamwidth of the radiated signal may be substantial, approaching as much as ninety degrees depending on the launch probe configuration, the energy that is actually propagated through the second aperture 125 has traveled the path generally defined by the arrow 127.

Although the absolute lateral separation between the apertures 126 and 125 is substantially equal to the diameter 133 of the cell 123, the total distance 173 traveled by the radiated energy through the process material is somewhat greater due to the longitudinal offset of apertures 126 and 125. The longer path length 173 corresponds to a longer residence time in the process material and contributes to a more accurate analysis of the process material properties.

In the particular offset arrangement shown the first aperture 126 is adjacent to the trailing edge 172 of the top plate 128 and the bottom plate 129, while the leading edge 171 of the top and bottom plates is adjacent to the second aperture 125. The width 132 of each aperture is approximately equal and substantially less than the total length 131 of the plates 128 and 129.

Figure 15:
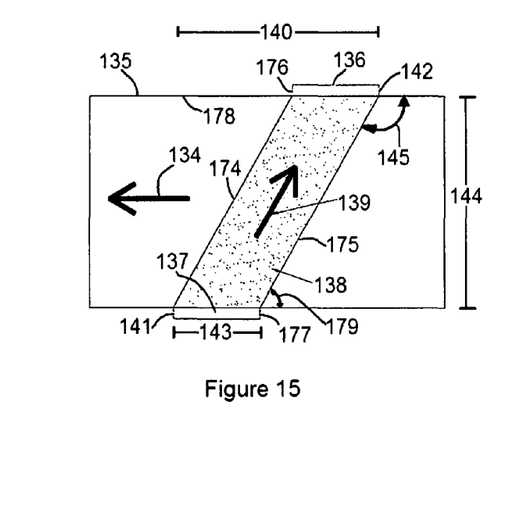
FIG. 15 is a top plan schematic view of a fourth embodiment of a cylindrical measurement cell constructed according to the principles of the present invention.
Figure 16:
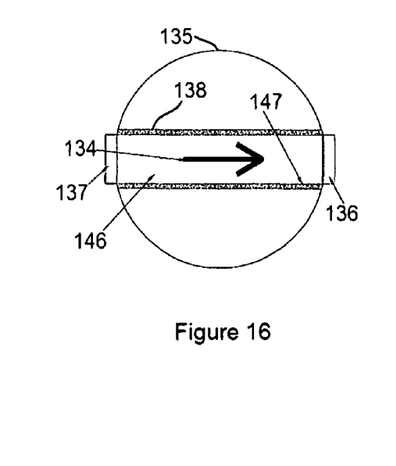
FIG. 16 is a side elevation schematic view of the cylindrical measurement cell depicted in FIG. 15.

Referring also to FIGS. 15 and 16, a second embodiment of an offset measurement cell 135 is depicted in which the launch aperture 137 is offset from the signal interception aperture 136. The cell 135 has a diameter 144 with spaced apart plates 138 and 147 defining a region 146 through which process material may flow in the direction of arrow 134. Further, the process material is free to flow above the upper plate 138 and below the lower plate 147. The radiated microwave energy used for performing the GMS analysis is defined by emissions traveling generally in the direction of arrow 139. In the case of process material flow in the direction of arrow 134, the leading edge 142 of aperture 136 is separated from the trailing edge 141 of aperture 137 by a distance 140. The distance 140 is typically at least twice as great as the width 143 of each aperture window. The leading edge 174 of each plate 138, 147 is defined by a straight line extending from the leading edge 141 of aperture 137 to the leading edge 176 of aperture 136. Similarly, the trailing edge 175 of each plate 138, 147 is defined by a straight line extending from the trailing edge 177 of aperture 137 to the trailing edge 142 of aperture 136. The trailing edge 175 forms an angle 145 with the sidewall 178 of cell 135, the angle 145 being greater than ninety degrees, with the complementary angle 179 being less than ninety degrees.

Figure 19:
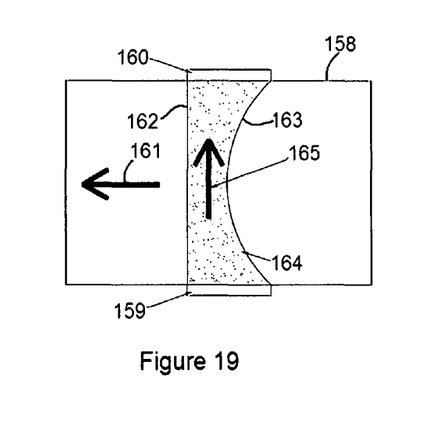
FIG. 19 is a top plan schematic view of a fifth embodiment of a cylindrical measurement cell constructed according to the principles of the present invention.
Figure 20:
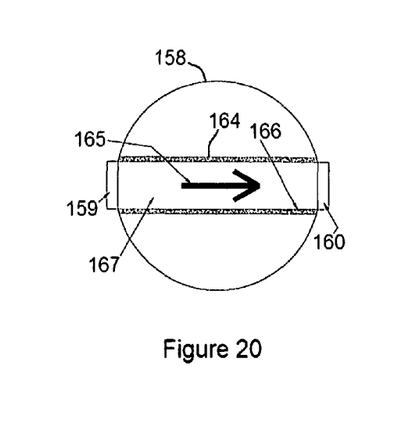
FIG. 20 is a side elevation schematic view of the cylindrical measurement cell depicted in FIG. 19.

As seen in FIGS. 19 and 20, the waveguide plates 164 and 166 may assume a nonrectangular geometry. The circular measurement cell 158 includes a launch aperture 159 and a reception aperture 160 which permit microwave energy to be radiated through the flowing process material generally in the direction of arrow 165, which is substantially perpendicular to the direction 161 of material flow. The trailing edge 162 of plates 164, 166 is defined as a straight line extending between the two apertures.

However, the leading edge 163 is defined by a curved line causing the plates 164, 166 to have a variable width. Such geometry would be appropriate for further reducing the frictional force experienced by a highly viscous flowable material.

The foregoing improvements embodied in the present invention are by way of example only. Those skilled in the field of guided microwave spectroscopy will appreciate that the foregoing features may be modified as appropriate for various specific applications without departing from the scope of the claims. For example, the location of the GMS cell 1 may be placed at many points in a continuous masa feed system. In a continuous system the cell can reside at the exit of masa extruder 16, at the inlet or exit of any pump used to transport the masa from the extruder 16, or anywhere along the pipe or series of pipes leading to the counter rotating sheeter assembly 120. While an eight inch diameter cell has been described in detail, any diameter may be selected as appropriate for a particular cell installation. Further, the dimensions given for various features of the invention are appropriate for the eight inch measurement cell but will of course vary when the cell 1 is of a differing diameter, length or geometry.

We claim:

1. A guided microwave spectroscopy system, comprising:
   (A) a cylindrical measurement cell, the cylindrical measurement cell comprising:
      (i) a first open end, the first open end being adapted to admit a product stream into the cylindrical measurement cell;
      (ii) a second open end, the second open end being adapted to discharge a product stream from the cylindrical measurement cell;
      (iii) a first plate, the first plate being substantially rigid and stationary, the first plate defining a first plane, the first plane being substantially parallel to a direction of product flow through the cylindrical measurement cell, the first plate further comprising:
         (a) a leading edge, the leading edge being formed as a bevel, the leading edge being oriented so as to cause the bevel to encounter the product stream before the product stream encounters any other portion of the first plate, the leading edge being formed as at least one of (i) a straight line and (ii) a curved line; and
         (b) a trailing edge;
      (iv) a second plate, the second plate being substantially rigid and stationary, the second plate defining a second plane, the second plane being substantially parallel to the first plane, wherein the first plate and the second plate have substantially identical dimensions, the first plate and the second plate being substantially parallel to a diameter of the cylindrical measurement cell, the first and second plate being positioned in an opposed relationship at a substantially equal distance from the diameter of the cylindrical measurement cell so as to define a waveguide region residing between the first and second plate;
   (B) a first microwave probe for radiating electromagnetic energy into the cylindrical measurement cell;
   (C) a second microwave probe for intercepting electromagnetic energy from within the cylindrical measurement cell; and
   (D) a path separator, the path separator causing a first portion of the product stream to pass completely through the cylindrical measurement cell and causing a second portion of the product stream to completely bypass the cylindrical measurement cell;
   (E) a substantially cylindrical outer casing forming part of the cylindrical measurement cell, the cylindrical outer casing comprising at least one orifice, the orifice being formed in the outer casing at a location outside of the waveguide region;
   (F) a telemetry sensor, the telemetry sensor being introduced into an interior region of the cylindrical measurement cell by extending through the orifice formed in the outer casing of the cylindrical measurement cell;
   (G) a first probe port, the first probe port being formed in the outer casing, the first probe port residing between the first and second plate so as to permit the first microwave probe to launch electromagnetic energy into the waveguide region, the first probe port having a fixed width and defining a first substantially rectangular plane, the first probe port having a leading edge, the first substantially rectangular plane being substantially perpendicular to the first plate and to the second plate;
   (H) a second probe port, the second probe port being formed in the outer casing, the second probe port residing between the first and second plate so as to permit the second microwave probe to intercept electromagnetic energy launched by the first microwave probe into the waveguide region, the second probe port having a trailing edge, the second probe port being longitudinally offset from the first probe port such that a distance between the leading edge of the first probe port and the trailing edge of the second probe port is at least twice as great as the fixed width of the first probe port.

2. The guided microwave spectroscopy system of claim 1, wherein the first plate is substantially narrower than the fixed width of the first probe port.

3. The guided microwave spectroscopy system of claim 1, wherein the first plate is formed to include a substantially curved leading edge and a substantially straight trailing edge.

4. A method of analyzing and adjusting the moisture content of a flowing high viscosity product stream traveling through a circular conduit, comprising the steps of:
   (a) affixing opposed, spaced apart substantially horizontal planar plates to an interior surface of the circular conduit so as to create a waveguide region residing between the planar plates;
   (b) forming opposed orifices within a first sidewall and a second opposed sidewall of the circular conduit;
   (c) affixing one of a first and second probe to each of the two opposed orifices so as to permit electromagnetic energy to be launched by the first probe through the waveguide region and to be intercepted by the second probe;
   (d) analyzing the electromagnetic energy within the waveguide region by means of guided microwave spectroscopy so as to determine the moisture content of the product stream;
   (e) beveling a leading edge of each horizontal planar plate so as to reduce discontinuities in flow velocity caused by impingement of the product stream on each plate; and
   (f) longitudinally offsetting the two opposed orifices such that a diametrical projection parallel to the planar plates of one orifice formed within the first sidewall onto the second opposed sidewall fails to overlap any portion of an opposed orifice formed within the second sidewall.

* * * * *